(12) United States Patent
Lucero et al.

(10) Patent No.: US 12,365,841 B2
(45) Date of Patent: Jul. 22, 2025

(54) PURIFICATION AND PROCESSING OF HYDROCARBON PRODUCTS

(71) Applicant: Agra Energy Holdings Corporation, Irvine, CA (US)

(72) Inventors: Andrew Lucero, Irvine, CA (US); Ravi Randhava, Irvine, CA (US); Anthony Long, Irvine, CA (US)

(73) Assignee: AGRA ENERGY HOLDINGS CORPORATION, Irvine, CA (US)

( * ) Notice: Subject to any disclaimer, the term of this patent is extended or adjusted under 35 U.S.C. 154(b) by 0 days.

(21) Appl. No.: 18/297,411

(22) Filed: Apr. 7, 2023

(65) Prior Publication Data

US 2023/0323217 A1  Oct. 12, 2023

Related U.S. Application Data

(60) Provisional application No. 63/362,694, filed on Apr. 8, 2022.

(51) Int. Cl.
| | |
|---|---|
| *C10G 2/00* | (2006.01) |
| *C07C 5/02* | (2006.01) |
| *C10G 45/58* | (2006.01) |

(52) U.S. Cl.
CPC ............... *C10G 45/58* (2013.01); *C07C 5/02* (2013.01); *C10G 2/30* (2013.01); *C10G 2300/1022* (2013.01); *C10G 2300/4006* (2013.01); *C10G 2300/4018* (2013.01); *C10G 2300/42* (2013.01)

(58) Field of Classification Search
CPC .. C10G 45/58; C10G 2/30; C10G 2300/1022; C10G 2300/4006; C10G 2300/4018; C10G 2300/42
See application file for complete search history.

(56) References Cited

U.S. PATENT DOCUMENTS

| | | | |
|---|---|---|---|
| 4,544,792 A | 10/1985 | Smith et al. | |
| 6,114,400 A * | 9/2000 | Nataraj | C01B 3/382 |
| | | | 518/703 |
| 10,144,000 B2 | 12/2018 | Goyal et al. | |
| 2007/0142481 A1* | 6/2007 | Steynberg | C10G 2/344 |
| | | | 518/726 |
| 2008/0312347 A1* | 12/2008 | Ernst | F25J 3/04563 |
| | | | 518/702 |
| 2015/0337212 A1 | 11/2015 | Hoek et al. | |
| 2015/0353837 A1* | 12/2015 | Fleys | C10G 2/32 |
| | | | 518/703 |

FOREIGN PATENT DOCUMENTS

WO  WO 2019/183444  9/2019

OTHER PUBLICATIONS

Written Opinon issued in Application No. PCT/US23/65523 dated Sep. 5, 2023.
International Search Report issued in Application No. PCT/US23/65523 dated Sep. 5, 2023.

* cited by examiner

*Primary Examiner* — In Suk C Bullock
*Assistant Examiner* — Jason Y Chong
(74) *Attorney, Agent, or Firm* — DLA PIPER LLP (US)

(57) ABSTRACT

Exemplary methods and systems for improved purification and processing of hydrocarbon products are provided.

4 Claims, 5 Drawing Sheets

PURIFICATION AND PROCESSING OF HYDROCARBON PRODUCTS

REFERENCE TO RELATED APPLICATIONS

This application claims priority to U.S. Provisional Application No. 63/362,694, filed Apr. 8, 2022, and entitled "Improved Purification and Processing of Hydrocarbon Products," which is hereby incorporated in its entirety by reference.

BACKGROUND

The GTL (gas to liquids) process is a refinery or conversion process to convert natural gas or other gaseous hydrocarbons into longer-chain hydrocarbons, such as gasoline or diesel fuel. The Fischer-Tropsch process is a GTL polymerization technique that turns a carbon source into hydrocarbons chains through the hydrogenation of carbon monoxide by means of a metal catalyst. The carbon source can be converted to synthesis gas (syngas) and the resulting syngas can be passed through a metal catalyst which causes polymerization into hydrocarbon products. The Fischer-Tropsch process also generates a by-product of tail gas stream, which is generally wasted.

What is needed is an improved process to purify hydrocarbon products from a Fischer-Tropsch tail gas stream.

BRIEF DESCRIPTION OF DRAWINGS

The foregoing summary and the following detailed description are better understood when read in conjunction with the appended drawings. Example embodiments are shown in the drawings; however, it is understood that the embodiments are not limited to the specific structures depicted herein. In the drawings.

DETAILED DESCRIPTION

The terminology used in the present disclosure is for the purpose of describing particular example embodiments only and is not intended to be limiting. As used in the description of the embodiments of the disclosure and the appended claims, the singular forms "a," "an," and "the" are intended to include the plural forms as well, unless the context clearly indicates otherwise.

The term "and/or," as used herein, refers to and encompasses any and all possible combinations of one or more of the associated listed items.

The term "about," as used herein when referring to a measurable value such as an amount of a component, time, temperature, and the like, is meant to encompass variations of 20%, 10%, 5%, 1%, 0.5%, or even 0.1% of the specified amount. Unless otherwise defined, all terms, including technical and scientific terms used in the description, have the same meaning as commonly understood by one of ordinary skill in the art to which this disclosure belongs.

In an embodiment, the present disclosure provides an improved process to purify hydrocarbon products from a Fischer Tropsch tail gas stream. In the processing of synthesis gas (syngas) to hydrocarbons, for example, in a Fischer Tropsch reactor, subsequent downstream flows can include both hydrocarbon products and unreacted gases. In cases where hydrocarbon products include both alkanes and alkenes, the alkene content can be subsequently processed in a downstream section of the physical plant.

In one embodiment, the present disclosure provides a process by which the conversion of alkenes, for example in a hydrocarbon stream, to alkanes using the full non-liquid gas stream from an upstream Fischer Tropsch reaction is achieved without gas separation. In an embodiment, the process of the present disclosure can lower the alkene content. In an embodiment, the process of the present disclosure can lower the alkene content to less than 1% via hydro-treating of the alkene content. In an embodiment, the present disclosure provides temperature and space velocity requirements for alkene conversion in the presence of mixed Fischer Tropsch tail gas stream.

Figure 1:
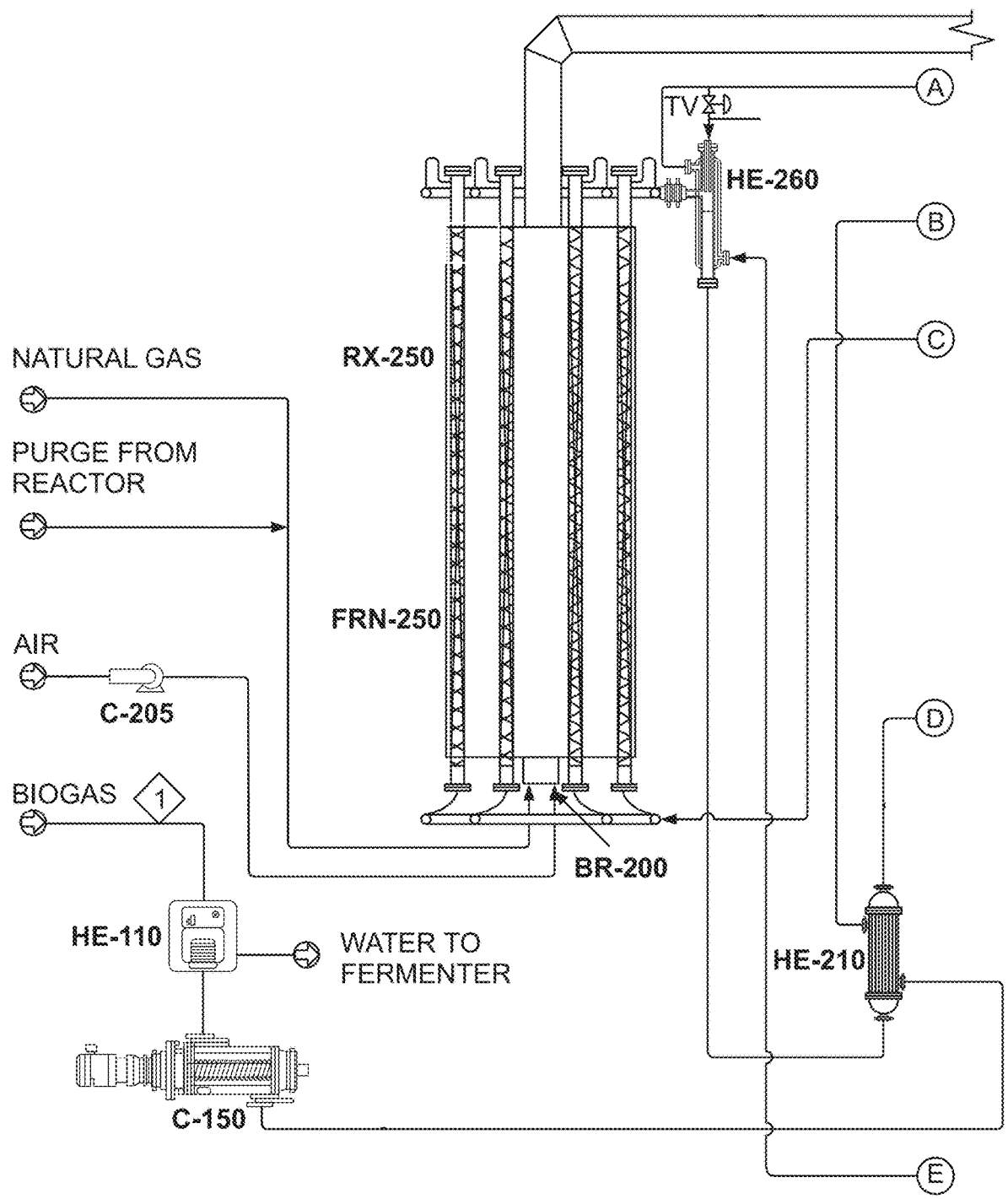
FIG. 1 is a flow diagram showing a process for converting natural gas and/or biogas into syngas, according to an exemplary embodiment of the present disclosure.
Figure 1:
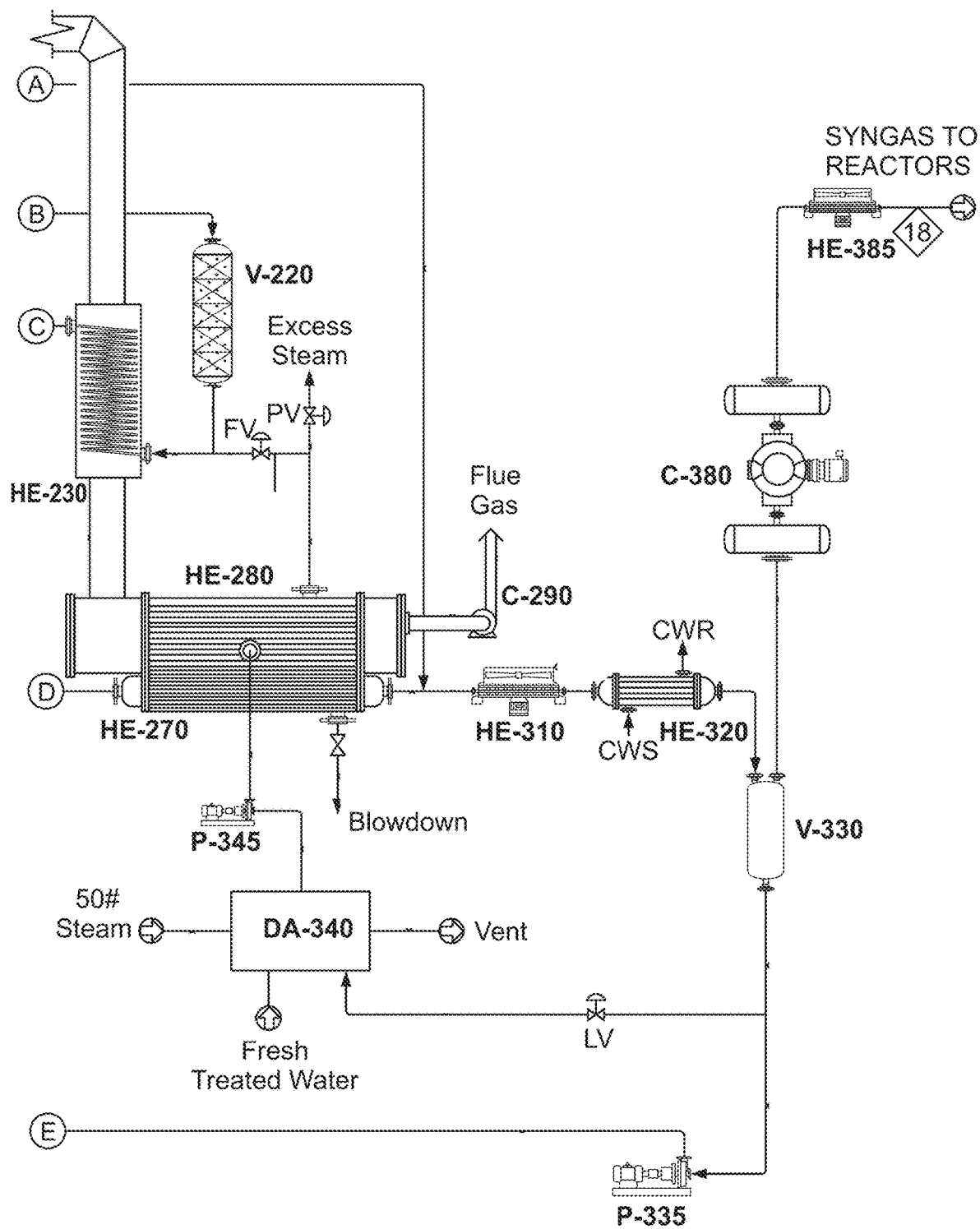

FIG. 1 is a flow diagram showing a process for converting natural gas and/or biogas into syngas, according to an exemplary embodiment of the present disclosure. Table 1 below identifies the component labels in FIG. 1 and the corresponding components:

TABLE 1

| Labels in FIG. 1 | Corresponding Components |
| --- | --- |
| C-205 | Air fan |
| HE-110 | Biogas dehumidifier |
| C-150 | Biogas compressor (175 HP) |
| RX-250 | Steam methane reformer |
| FRN-250 | Steam reformer furnace |
| BR-200 | Burner |
| HE-260 | Desuperheater |
| HE-210 | Biogas heater |
| HE230 | Mixed feed heater |
| HE270 | Heat recovery boiler |
| V-220 | Desulfurizer |
| HE-280 | Waste heat boiler |
| P-345 | Boiler feedwater (BFW) pump |
| DA-340 | Deaerator |
| HE-310 | Syngas air cooler |
| C-290 | Extraction fan |
| HE-320 | Syngas cooler |
| V-330 | Condensate KO receiver |
| P-335 | Condensate pump |
| C-380 | Syngas compressor (100 HP) |
| HE-385 | Compressed syngas cooler |
| CWS | Chilled water supply |
| CWR | Chilled water return |

Figure 2:
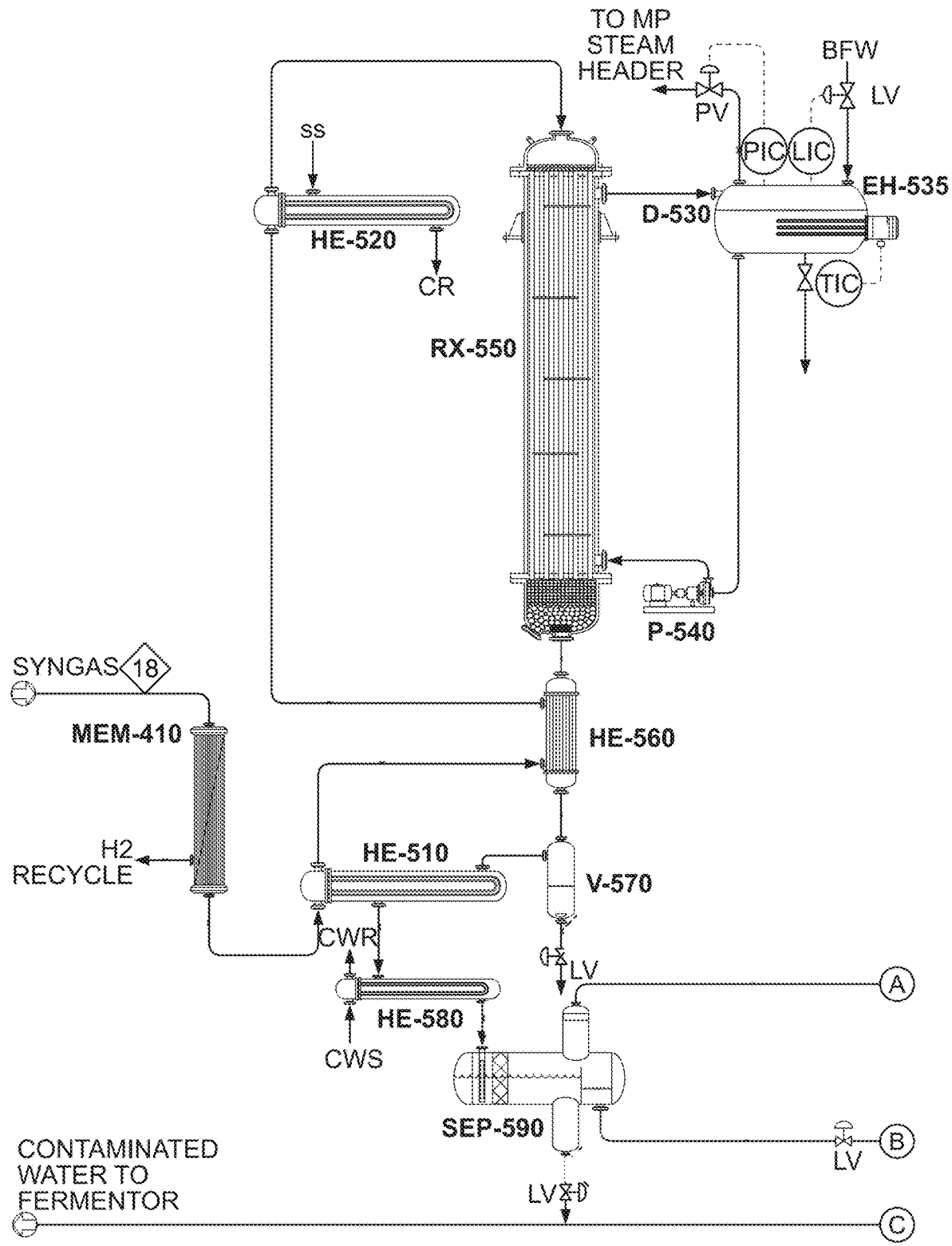
FIG. 2 is a flow diagram showing a process for converting syngas into hydrocarbon product, according to an exemplary embodiment of the present disclosure.
Figure 2:
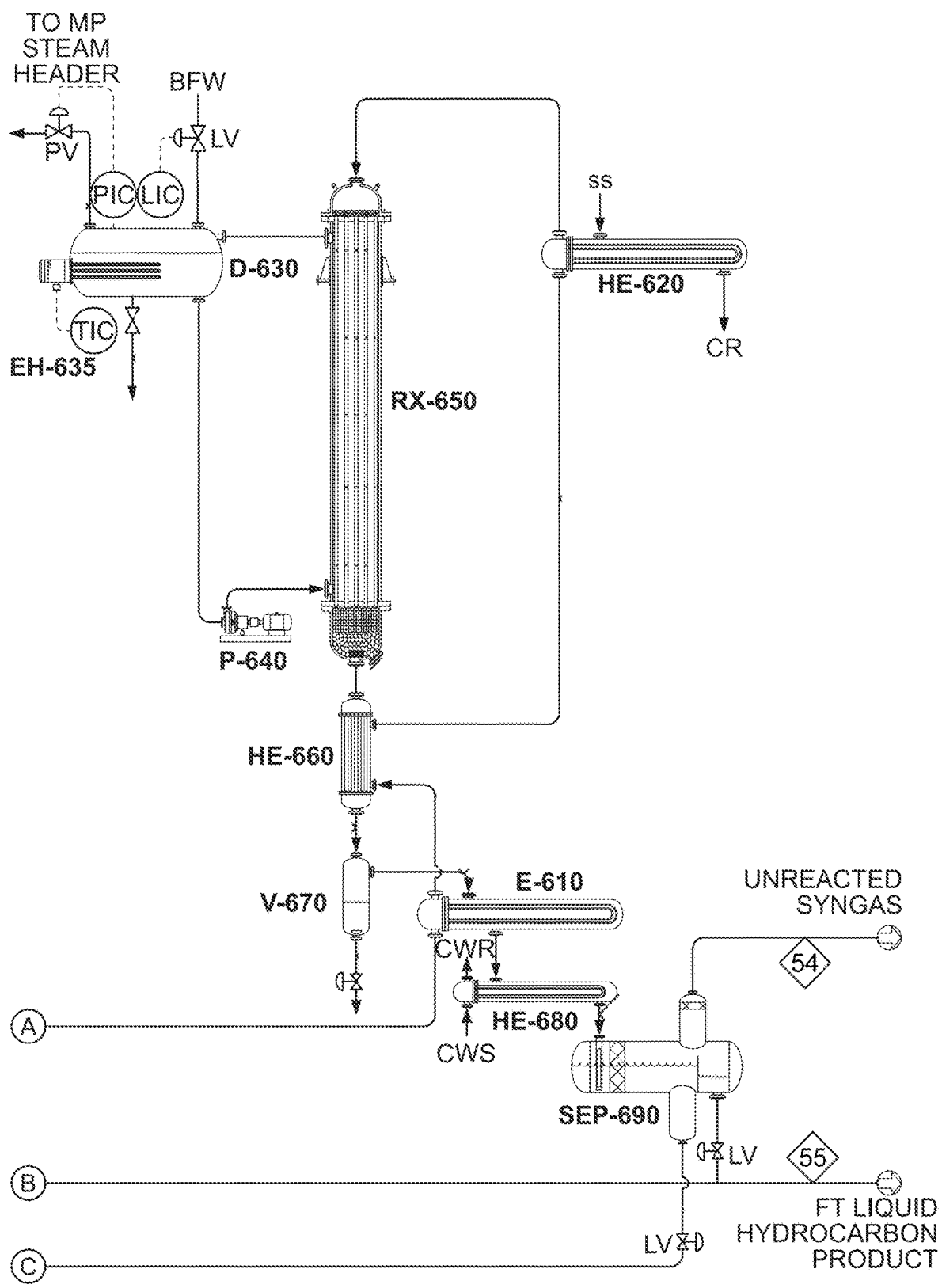

FIG. 2 is a flow diagram showing a process for converting syngas into hydrocarbon product, according to an exemplary embodiment of the present disclosure. Table 2 below identifies the component labels in FIG. 2 and the corresponding components:

TABLE 2

| Labels in FIG. 2 | Corresponding Components |
| --- | --- |
| MEM-410 | $H_2$ depleting membrane |
| HE-520 | Steam preheater |
| HE-510 | Reactor interchanger |
| HE-580 | Cooler |
| SEP-590 | Gas-liquid-liquid separator |
| V-570 | Wax separator |
| RX-550 | $1^{st}$ stage Fischer Tropsch reactor |
| HE-560 | Effluent cooler |

TABLE 2-continued

| Labels in FIG. 2 | Corresponding Components |
| --- | --- |
| P-540 | Reactor water pump |
| D-530 | Reactor steam drum |
| EH-535 | Start-up heater |
| EH-635 | Start-up heater |
| D-630 | Reactor stream drum |
| RX-650 | $2^{nd}$ stage Fischer Tropsch reactor |
| P-640 | Reactor water pump |
| HE-660 | Effluent cooler |
| V-670 | Wax separator |
| HE-680 | Cooler |
| E-610 | Reactor product interchanger |
| HE-620 | Steam preheater |
| SEP-690 | Gas-liquid-liquid separator |

Figure 3:
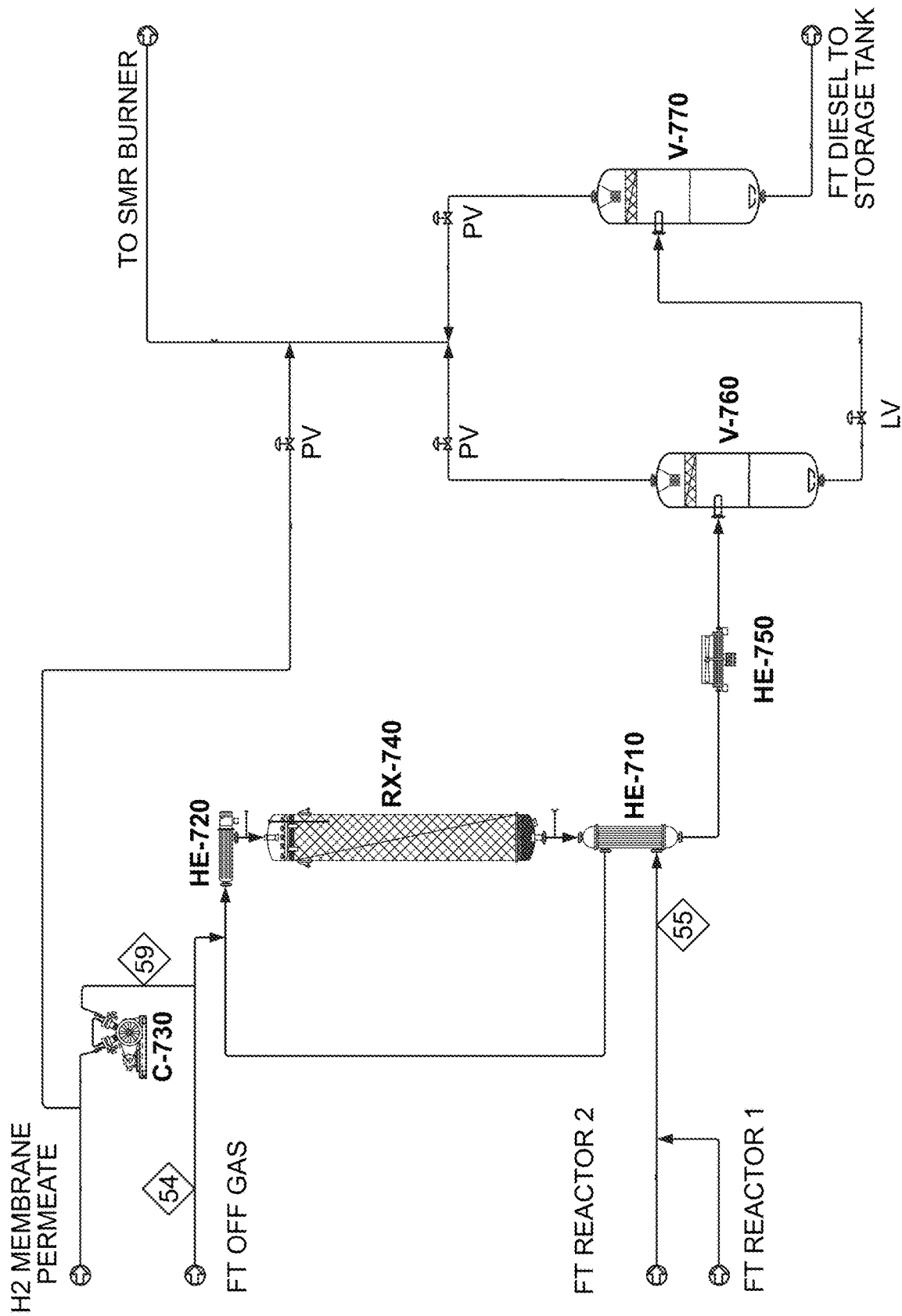
FIG. 3 is a flow diagram showing a process for converting unreacted off gas into diesel, according to an exemplary embodiment of the present disclosure.

FIG. 3 is a flow diagram showing a process for converting unreacted off gas into diesel, according to an exemplary embodiment of the present disclosure. Table 3 below identifies the component labels in FIG. 3 and the corresponding components:

TABLE 3

| Labels in FIG. 3 | Corresponding Components |
| --- | --- |
| C-730 | $H_2$ compressor |
| HE-720 | Feed trim heater |
| RX-740 | Olefin hydrogenation reactor |
| HE-710 | Hydrogenator preheater |
| HE-750 | Hydrogenator cooler |
| V-760 | HP diesel separator |
| V-770 | LP diesel separator |

In an embodiment, flow #54 in FIGS. 1-3 show a process of the present disclosure. In one embodiment, in the processing of synthesis gas (flow #18 in FIGS. 1-3) to hydrocarbons in a Fischer Tropsch (FT) reactor, subsequent downstream flows can include both hydrocarbon products (flow #55 in FIGS. 1-3) and unreacted gases (flow #54 in FIGS. 1-3). In cases where hydrocarbon products include both alkanes and alkenes, the alkene content may be subsequently processed in a downstream section of the physical plant (RX-740 in FIG. 3). In an embodiment, flow #54 and zero flow #59 in FIGS. 1-3 show a process by which the conversion of alkenes in a hydrocarbon stream to alkanes can be achieved using the full non-liquid gas stream from an upstream FT reaction without gas separation. In an embodiment, the process of the present disclosure can lower the alkene content. In an embodiment, the process of the present disclosure can lower the alkene content to less than 1% via hydro-treating of the alkene content.

In an embodiment, the present disclosure can provide temperature and space velocity requirements for alkene conversion in the presence of mixed FT tail gas stream, all occurring in RX-740 (FIG. 3).

Certain process flows may have only the compressed H2 (flow #59 in FIGS. 1-3) going to the hydrotreating process, with little to none tail gases (flow #54 in FIGS. 1-3). In an embodiment, the present disclosure provides a system that can take in non-separated biogas (flow #1 in FIGS. 1-3) and can process it with a steam methane reformer (RX-250 in FIG. 1) to become synthesis gas (flow #18 in FIGS. 1-3). The synthesis gas can be reacted via Fischer Tropsch (RX-550 in FIG. 2) to produce hydrocarbon liquids (flow #55 in FIGS. 1-3) and unreacted gases (flow #54 in FIGS. 1-3). The hydrocarbon stream may be hydrotreated, which can be accomplished in (RX-740 in FIG. 3). The present disclosure provides a unique process to use tail gases (flow #54 in FIGS. 1-3) from the FT reactor, compared to a separated compressed H2 flow (flow #59 in FIGS. 1-3).

While the present disclosure has been discussed in terms of certain embodiments, it should be appreciated that the present disclosure is not so limited. The embodiments are explained herein by way of example, and there are numerous modifications, variations and other embodiments that may be employed that would still be within the scope of the present disclosure.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. The examples set forth in this document are for illustrative purposes and all elements of the example may not be required or exhaustive. Accordingly, other implementations are within the scope of the following claims. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter. For example, the steps and/or limitations in the specification, drawings, and/or claims may be performed in an order other than the order set forth in the specification, drawings, and/or claims.

In addition, it should be understood that any figures which highlight the functionality and advantages are presented for example purposes only. The disclosed methodology and system are each sufficiently flexible and configurable such that they may be utilized in ways other than that shown. For example, other steps may be provided, or steps may be eliminated, from the described flows, and other components may be added to, or removed from, the described systems.

Although the term "at least one" may often be used in the specification, claims and drawings, the terms "a", "an", "the", "said", etc. also signify "at least one" or "the at least one" in the specification, claims and drawings.

Finally, it is the applicant's intent that only claims that include the express language "means for" or "step for" be interpreted under 35 U.S.C. 112(f). Claims that do not expressly include the phrase "means for" or "step for" are not to be interpreted under 35 U.S.C. 112(f).

We claim:

1. A method comprising:
   subjecting syngas to a Fischer Tropsch reaction to produce a Fischer Tropsch effluent;
   separating the Fischer Tropsch effluent in a gas-liquid-liquid separator into a full non-liquid tail gas stream comprising unconverted syngas, a hydrocarbon liquid stream, and a water stream;
   passing the hydrocarbon liquid stream and the full non-liquid tail gas stream to a hydrogenation reactor to produce a hydrogenation effluent, wherein alkenes in the hydrocarbon liquid stream are converted into alkanes in the hydrogenation reactor and wherein the full non-liquid tail gas stream is directly sent from the gas-liquid-liquid separator to the hydrogenation reactor without a compositional gas separation; and obtaining a diesel fuel stream from the hydrogenation effluent.

2. The method of claim 1, wherein the alkene content in the hydrocarbon liquid stream is lowered via the conversion of the alkenes to alkanes.

3. The method of claim 1, wherein the alkene content in the hydrocarbon liquid stream is lowered to less than 1% via hydro-treating of the full non-liquid gas to convert alkenes to alkanes.

4. The method of claim 1, the alkene conversion being based on temperature and space velocity requirements in a presence of the full non-liquid tail gas stream.

* * * * *